United States Patent [19]

Johnson

[11] 4,059,435

[45] Nov. 22, 1977

[54] HERBICIDAL 4-TRIFLUOROMETHYL-3-CYANOALKOXY-4-NITRO DIPHENYL ETHERS

[75] Inventor: Wayne O. Johnson, Warminster, Pa.

[73] Assignee: Rohm and Haas Company, Philadelphia, Pa.

[21] Appl. No.: 719,471

[22] Filed: Aug. 31, 1976

[51] Int. Cl.$^2$ .................. C07C 121/66; A01N 9/20
[52] U.S. Cl. ......................................... 71/105; 71/88; 71/90; 71/92; 71/93; 71/97; 71/98; 71/100; 71/106; 71/107; 71/108; 71/109; 71/110; 71/113; 71/115; 71/116; 71/117; 71/118; 71/119; 71/120; 71/122; 71/124
[58] Field of Search ................... 260/465 F; 71/105

[56] References Cited

U.S. PATENT DOCUMENTS

| | | | |
|---|---|---|---|
| 3,467,692 | 9/1969 | Newallis et al. | 260/465 F |
| 3,928,416 | 12/1975 | Bayer et al. | 71/105 X |

*Primary Examiner*—Joseph Paul Brust
*Attorney, Agent, or Firm*—William E. Lambert, III

[57] ABSTRACT

Compounds of the formula

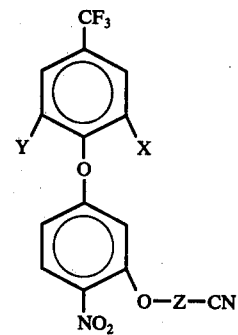

wherein
X is a hydrogen atom, a halogen atom, a trihalomethyl group, an alkyl group, or a cyano group,
Y is a hydrogen atom, a halogen atom, or a trihalomethyl group, and
Z is a divalent alkylene group, and compositions containing these compounds exhibit herbicidal activity.

12 Claims, No Drawings

HERBICIDAL 4-TRIFLUOROMETHYL-3-CYANOALKOXY-4-NITRO DIPHENYL ETHERS

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

In accordance with the present invention, there is provided a new class of novel diphenyl ethers having the formula

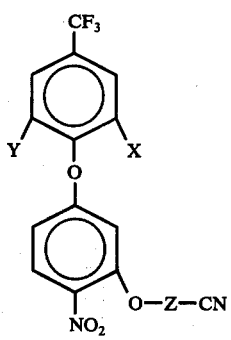

wherein
X is a hydrogen atom, a halogen atom, preferably a fluorine atom or a chlorine atom, a trihalomethyl group, preferably a trifluoromethyl group, a (C₁-C₄)alkyl group, preferably a methyl group, or a cyano group,
Y is a hydrogen atom, a halogen atom, preferably a fluorine atom or a chlorine atom, or a trihalomethyl group, preferably a trifluoromethyl group, and
Z is a (C₁-C₄)divalent alkylene group, having either a straight- or branched-chain configuration.

These novel compounds have been found to show unexpected activity as weed control agents. In a preferred embodiment of the invention, X is a halogen atom, most preferably a chlorine atom, Y is a hydrogen atom or a halogen atom, most preferably a chlorine atom, and Z has the formula

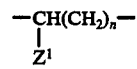

wherein $Z^1$ is a hydrogen atom or $(C_1-C_3)$alkyl group, and $n$ is 0 or 1. The most preferred embodiment is that in which $Z^1$ is a methyl group and $n$ is 0.

Examples of the compounds of the invention embraced by Formula I include:

2-Chloro-α,α,α-trifluoro-p-tolyl-3-(1-cyanomethoxy)-4-nitrophenyl ether
2-Cyano-α,α,α-trifluoro-p-tolyl-3-(1-cyanoethoxy)-4-nitrophenyl ether
2-Chloro-6,α,α,α-tetrafluoro-p-tolyl-3-(2-cyanopropoxy)-4-nitrophenyl ether
α,α,α,α',α',α'-Hexafluoro-2,4-xylyl-3-(1-cyanoethoxy)-4-nitrophenyl ether
2,6-Dichloro-α,α,α-trifluoro-p-tolyl-3-(4-cyanobutoxy)-4-nitrophenyl ether
6-Chloro-2-methyl-α,α,α-trifluoro-p-tolyl-3-(2-cyanoethoxy)-4-nitrophenyl ether
2-Chloro-α,α,α-trifluoro-p-tolyl-3-(1-cyanoethoxy)-4-nitrophenyl ether
α,α,α-Trifluoro-p-tolyl-3-(1-cyanoethoxy)-4-nitrophenyl ether
2-Cyano-6-chloro-α,α,α-trifluoro-p-tolyl-3-(1-cyanoisopropoxy)-4-nitrophenyl ether The novel diphenyl ethers of the invention are useful both as preemergence and as postemergence herbicides. Preemergence herbicides are ordinarily used to treat the soil in which the desired crop is to be planted by application either before seeding, during seeding, or, as in most application, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, safflower, beans, peas, carrots, corn, wheat and other cereal crops.

Diphenyl ethers of the invention are useful for controlling weeds in rice crops. When used in transplanted rice crops, the ethers can be applied either preemergence or postemergence to the weeds — that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in post-emergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts or alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 29% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grainhulls, or similar material. A solution of one or more of the diphenyl ethers in a volatile organic solvent then removed by evaporation. The granular material can have any suitable size, wiith a preferably size range of 16 to 60 mesh. The diphenyl ether will usually comprise about 2 to 15% of the granular formulation.

The diphenyl ethers of the invention can also be mixed with fertilizers for fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts 2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino)-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-ethoxy-4'-nitrodiphenyl ether
2-chloro-4-trifluoromethyl-4'-nitrodiphenyl ether
2-chloro-4-trifluoromethyl-3'-carbethoxy-4'-nitrodiphenyl ether
2,4-dichloro-3'-carbomethoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trifmethylacetamide
N-(3,4-dichlorophenyl)-$\alpha,\alpha$-dimethylvaleramide
N-(isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-$\alpha,\alpha$-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
0-(2,4-dichlorophenyl)-0-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiazidzin-(4)3H-one-2,2-dioxide
6,7-dihydrodipyridol[1,2-a:2',1'-c]pyrazidinium salts
1,1'-dimethyl-4,4'bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The ethers of the invention can be prepared by reacting a diphenyl ether of the formula

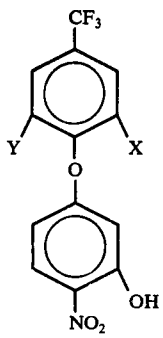

wherein X and Y are as defined above, with an α-halonitrile in the presence of an acid scavenger, such as potassium hydroxide, potassium carbonate, or the like. The reaction can be carried out in any solvent in which the reactants are at least partially soluble, including such solvents as diverse as glyme and dimethylsulfoxide. The reaction is generally carried out at a temperature of about 0° to about 200° C, preferably about 20° to about 100° C, with reaction times appropriate to the reaction conditions selected.

In an alternative preparative procedure, the compounds of the invention can be prepared from the same starting material in a multi-step sequence in which the nitrophenol is condensed either with an α-haloacid, amide or ester, under similar conditions to those for the nitrile. The ester can then be hydrolyzed with acidic or, preferably, basic catalysis to give the acid. The acid can then be converted to the acid chloride, for example with thionyl chloride, which on treatment with ammonia gives the amide. This amide, on treatment with dehydrating agents, such as, for example, phosphorus oxychloride, will yield the desired nitrile.

Ethers of the invention can also be prepared by reacting a diphenyl ether precursor of the formula

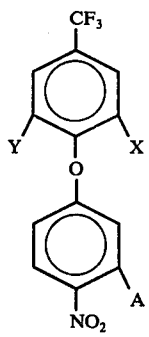

wherein
A is a good leaving group, such as a halogen atom, preferably a chlorine atom, a substituted phenoxy group, such as a 2-chloro-4-trifluoromethyl-phenoxy group, or the like,
with an appropriate substituted carbinol of the formula

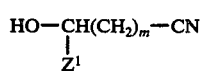

wherein $Z^1$ is as defined above and $m$ is 1, 2, or 3. This reaction is generally carried out at a temperature of about 0° to about 200° C, and preferably about 20° to about 120° C. The reaction can be carried out in any inert solvent in which the reactants are at least partially soluble. The preferred solvents are nonpolar aprotic solvents, such as benzene, dioxane, and the like.

Ethers of the invention can also be prepared by condensing a suitably-substituted phenol, for example 2-chloro-4-trifluoromethyl phenol, with a suitably substituted nitrobenzene, such as 3-(2-cyanoethoxy)-4-nitro fluorobenzene, in the presence of an alkaline agent, such as potassium hydroxide or carbonate, in an aprotic, preferably polar sovent, such as dimethylsulfoxide.

In some cases it can be advantageous to add the nitro group after formation of the diphenyl ether and build-up of the cyanoalkoxy sidechain. Thus, for example, resorcinol may be condensed with 3,4-dichlorobenzotrifluoride in the presence of base to give 2-chloro-4-trifluoromethylphenyl-3-hydroxyphenyl ether. This intermediate can be condensed, as described above, with, for example, an α-halo nitrile and the product then nitrated.

Further, other manipulations of the sidechain before or after nitration can provide ethers of the invention. Thus, for example, a halogen atom, preferably bromine may be introduced into the sidechain by any of a number of standard techniques, for example, condensation of a halogen containing group with any of the above described intermediates. The halogen atom may then be directly replaced by a nitrile group by nucleophilic displacement using standard techniques.

The diphenyl ether precursors can be prepared by reacting a suitably substituted phenol, or the potassium or sodium salt of the phenol, with a suitably substituted halobenzene, such as a chloro- or fluorobenzene in the presence of an alkaline agent. Such precursors and their preparation are described in U.S. Pat. No. 3,928,416, of Bayer et al., granted Dec. 23, 1975, which is incorporated herein by reference.

The following examples will further illustrate this invention but are not intended to limit it in any way. All temperatures are in degrees Centigrade and parts and percentages are by weight unless otherwise indicated.

EXAMPLE 1

Preparation of 2-Chloro-ααα-trifluoro-p-tolyl-3-α-cyanomethoxy-4-nitrophenyl ether A mixture of 2-chloro-ααα-trifluoro-p-tolyl-3-hydroxy-4-nitrophenyl ether (16.65 0.05 mole), and potassium carbonate (10.40 g., 0.075 mole) in dimethyl sulfoxide (25 ml) is stirred at room temperature until evolution of carbon dioxide ceases, then α-chloro acetonitrile (3.75g, 0.05 mole) is added and the mixture stirred overnight at room temperature, then 20 hours at 45° C. The mixture is diluted with water and extracted with carbon tetrachloride. The extract is washed with water, dried and the solvent removed to give 9.8 g of 2-chloro-ααα-trifluoro-p-tolyl-3-α-cyanomethoxy-4-nitrophenyl ether as a dark yellow oil which is not purified further. Analysis: Found (req.) C, 48.07(48.34); H, 2.16(2.16); N, 7.22(7.51); Cl, 9.46 (9.51); F, 15.66(15.29).

EXAMPLE 2

Preparation of 2-Chloro-ααα-trifluoro-p-tolyl-3-α-cyanoethoxy-4-nitrophenyl ether A solution of 2-chloro-ααα-trifluoro-p-tolyl-3-(1-carbamoylethoxy)-4-nitro phenyl ether (5 g) in benzene (100 ml) is heated with phosphorus oxychloride (5 g) for 6 hours at 80° C and stood 3 days at 45° C. The solution is diluted with ether, washed with water and the solvents removed. The residue is extracted into boiling hexane by decantation and the solvent removed. The residue is recrystallized from isopropanol to give 2-chloro-α,α,α-trifluoro-p-tolyl-3-α-cyano ethoxy)-4-nitrophenyl ether m.p. 75°-77° C. Analysis: Found (req.) C, 49.55(46.69); H, 2.44(2.61); N, 6.87(7.25); Cl, 9.16(9.17); F, 14.22(14.74).

EXAMPLES 3 TO 7

Following the procedures set forth above with appropriate starting materials, the following compounds can be prepared:

2-Cyano-α,α,α-trifluoro-p-tolyl-3-α-cyanoethoxy-4-nitrodiphenyl ether
2-Cyano-6,α,α,α-tetrafluoro-p-tolyl-3-α-cyanoethoxy-4-nitrodiphenyl ether
2-Chloro-α,α,α-trifluoro-p-tolyl-3-α-cyanopropoxy-4-nitrophenyl ether
α,α,α-Trifluoro-p-tolyl-3-α-cyanomethoxy-4-nitrohenyl ether
2-Chloro-α,α,α-trifluoro-p-tolyl-3-α-cyanoethoxy-4-nitrophenyl ether The following examples show the herbicidal properties of diphenyl ethers of the invention.

EXAMPLE 8

This example shows the herbicidal activity of diphenyl ethers of the invention towards a number of common weeds. Using the procedure described below, diphenyl ethers were evaluated for control of the following weeds:

Monocots (M)

barnyardgrass (*Echinochloa crusgalli*)
Bermudagrass (*Cynodon dactylon*)
crabgrass (*Digitaria spp.*)
foxtail (*Setaria faberii*)
Johnsongrass (*Sorghum halepense*)
nutsedge (*Cyperus esculentus*)
quackgrass (*Agropyron repens*)

Dicots (D)

bindweed (*Convolvulus arvensis*)
cocklebur (*Xanthium pensylvanicum*)
coffeeweed (*Sesbania macrocarpa*)
morningglory (*Ipomoea purpurea*)
ragweed (*Ambrosia artemisiifolia*)
tomato (*Lycopersicon esculentum*)
velvetleaf (*Abutilon theohrasti*)

The following test procedure is employed. Seeds of selected crops and weeds are planted in soil in flats. For preemergence tests, the flats are treated with the test compound immediately after the planting. For postemergence tests, the seeds are allowed to germinate, and after 2 weeks the flats are treated with the test compound immediately after the planting. For postemergence tests, the seeds are allowed to germinate, and after 2 weeks the flats are treated with the test compound. The compound to be evaluated is dissolved in acetone, diluted with water, and sprayed over the flats using a carrier volume equivalent to 50 gallons per acre at the rate of application of 2 pounds per acre. About 2 weeks after the application of the test compound, the state of growth of the plants is observed and the phytotoxic effect of the compound is evaluated. Table II gives the average percent control achieved by the test compounds in terms of the percent of the plants which are killed by the compounds.

TABLE II

| Compound of Example No. | lb./A. | HERBICIDAL ACTIVITY (% control) Preemergence 2 | Postemergence 2 |
|---|---|---|---|
| 1 | M | 78 | 84 |
|   | D | 50 | 100 |
| 2 | M | 76 | 46 |
|   | D | 87 | 100 |

It is to be understood that changes and variations can be made without departing from the spirit and scope of the invention as defined by the appended claims.

I claim:

1. A compound of the formula

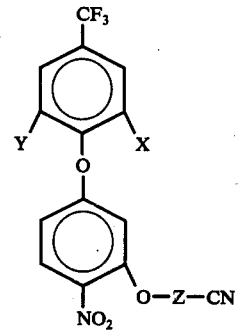

wherein
X is a hydrogen atom, a halogen atom, a trifluoromethyl group, a (C₁-C₄)alkyl group, or a cyano group,
Y is a hydrogen atom, a halogen atom, or a trifluoromethyl group, and
Z is a divalent (C₁-C₄)alkylene group.

2. The compound of claim 1 wherein Y is a hydrogen atom.

3. The compound of claim 2 wherein X is a halogen atom.

4. The compound of claim 3 wherein Z has the formula

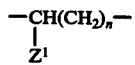

wherein
Z¹ is a hydrogen atom or (C₁-C₃)alkyl group and n is 0 or 1.

5. The compound of claim 4 wherein X is a chlorine atom, Z¹ is a hydrogen atom, and n is 1.

6. The compound of claim 4 wherein X is a chlorine atom, Z¹ is a methyl group, and n is 0.

7. A herbicidal composition which comprises a compound according to claim 1 and an agronomically-acceptable carrier.

8. The composition of claim 7 which additionally comprises a surfactant.

9. A method of controlling weeds which comprises applying to the surface of the growth medium prior to the emergence of the weeds from the growth medium a compound of claim 1 in an amount effective to control the growth of the weeds.

10. The method of claim 9 wherein the compound is applied in an amount of about 0.1 to about 12 pounds per acre.

11. A method of controlling weeds which comprises applying to weed seedlings a compound of claim 1 in an amount sufficient to control the growth of the seedlings.

12. The method of claim 11 wherein the compound is applied in an amount of about 0.1 to about 12 pounds per acre.

* * * * *